United States Patent
Siochi

(12) 
(10) Patent No.: US 6,473,490 B1
(45) Date of Patent: Oct. 29, 2002

(54) INTENSITY MAP RECONSTRUCTION FOR RADIATION THERAPY WITH A MODULATING MULTI-LEAF COLLIMATOR

(75) Inventor: Ramon Alfredo Carvalho Siochi, Apex, NC (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/967,618

(22) Filed: Sep. 28, 2001

(51) Int. Cl.[7] .................................................. A61N 5/10
(52) U.S. Cl. .......................................... 378/65; 378/95
(58) Field of Search .............................. 378/64, 65, 95

(56) References Cited

U.S. PATENT DOCUMENTS

| | | | |
|---|---|---|---|
| 5,663,999 A | 9/1997 | Siochi | 378/65 |
| 5,724,403 A | 3/1998 | Siochi et al. | 378/150 |
| 6,052,435 A * | 4/2000 | Hernandez-Guerra et al. | 250/492.1 |
| 6,108,400 A | 8/2000 | Siochi | 378/65 |
| 6,128,366 A | 10/2000 | Siochi | 378/65 |
| 6,134,296 A | 10/2000 | Siochi | 378/65 |
| 6,142,925 A * | 11/2000 | Siochi et al. | 600/1 |
| 6,167,114 A | 12/2000 | Siochi | 378/65 |
| 6,240,162 B1 * | 5/2001 | Hernandez-Guerra et al. | 378/108 |

* cited by examiner

Primary Examiner—David V. Bruce

(57) ABSTRACT

A method for reconstructing an intensity map from segments includes importing a set of segments defining an intensity modulated radiation treatment and analyzing the segments to determine intensity map geometry. The method further includes calculating radiation contributions for cells within the segments and creating a reconstructed intensity map.

17 Claims, 5 Drawing Sheets

INTENSITY MAP RECONSTRUCTION FOR RADIATION THERAPY WITH A MODULATING MULTI-LEAF COLLIMATOR

FIELD OF THE INVENTION

The present invention relates generally to radiation therapy, and more particularly, to a method and system for reconstructing an intensity map from segments defining an intensity modulation radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

Many conventional treatment planning systems do not export intensity maps, but instead export only segments defining an intensity modulated radiation treatment. However, software used with radiation therapy equipment often requires an intensity map. The systems may calculate intensity maps from their internally generated segments, however, this is done only for comparison with the original intensity map in order to perform fluence correction to minimize the difference between the original intended map and the actual deliverable map. These systems are not designed to create an importable intensity map from an external source of segments. Furthermore, conventional systems can not communicate with other planning systems that only produce segments for the purpose of creating intensity maps and creating a more efficient set of segments. These systems may import segments, but only for the purpose of doing a direct dose distribution calculation, and not for the purpose of creating a new intensity map that can be used to create new segments. Conventional treatment planning systems that do not export intensity maps are not able to take advantage of the segmentation capabilities of software such as IMFAST (available from Siemens Corporation), since this software performs segmentation starting from intensity maps.

Accordingly, there is therefore, a need for a system and method that reconstructs intensity maps from imported segments to allow for the exchange of intensity maps indirectly by exchanging segments.

SUMMARY OF THE INVENTION

A method and system for reconstructing an intensity map from segments are disclosed.

A method for reconstructing an intensity map generally comprises importing a set of segments and analyzing the segments to determine intensity map geometry. Radiation contributions are calculated for each cell in each of the segments and a reconstructed intensity map is created.

A system for reconstructing an intensity map generally comprises a processor configured to import a set of segments from a treatment planning system and operable to analyze the segments to determine intensity map geometry, calculate radiation contributions for each cell in each of the segments, and create a reconstructed intensity map. The system further includes memory operable to at least temporarily store the segments.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
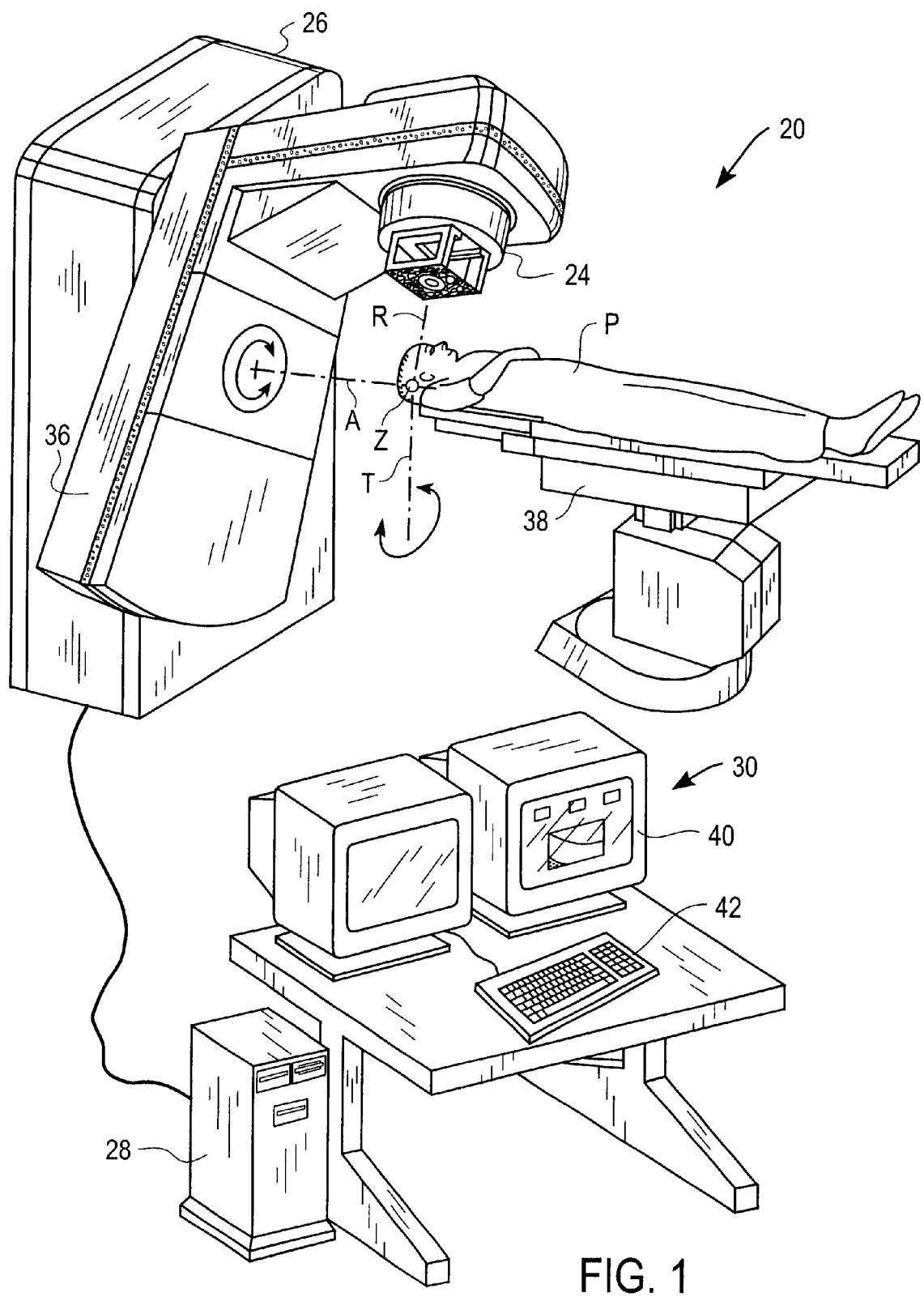
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
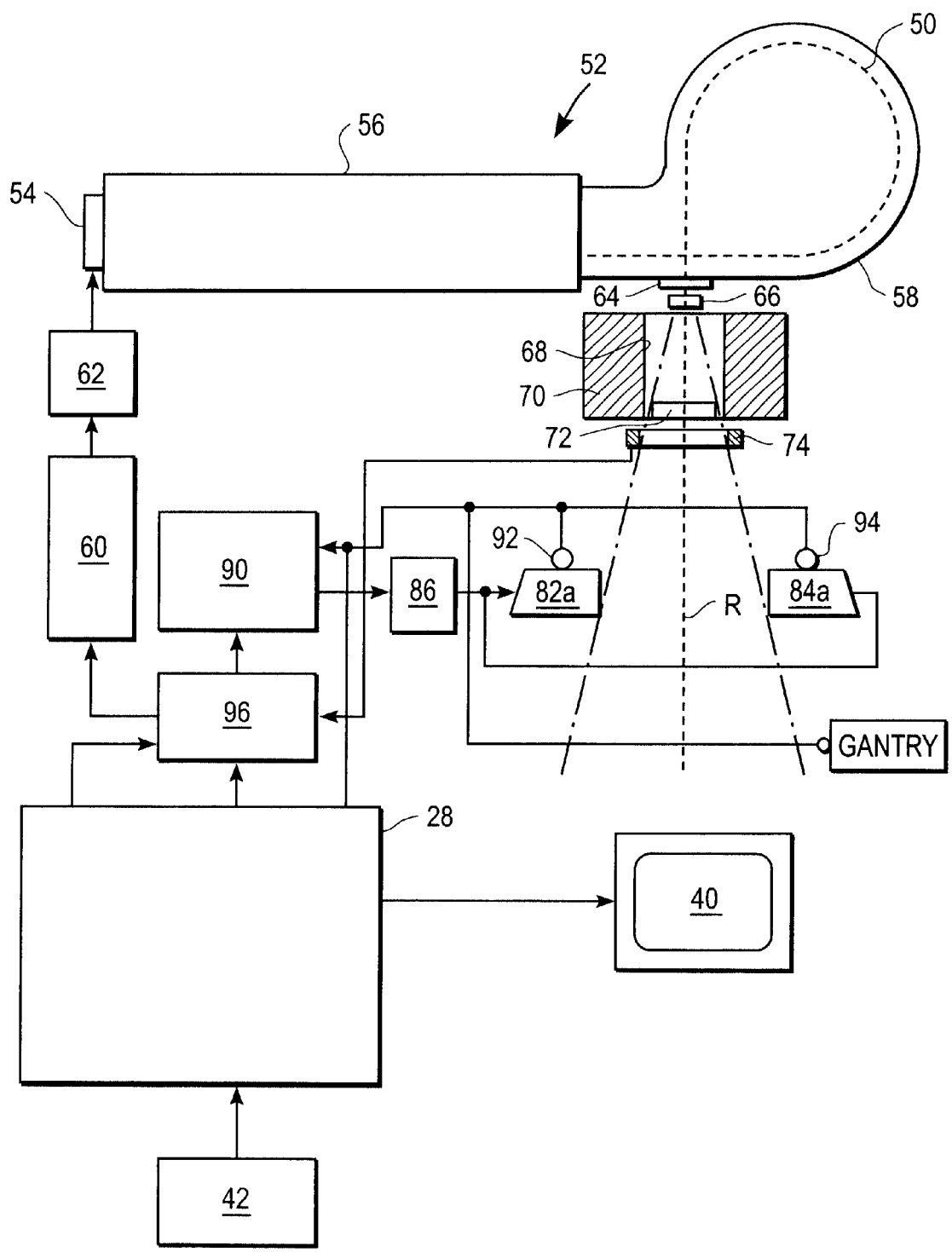
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
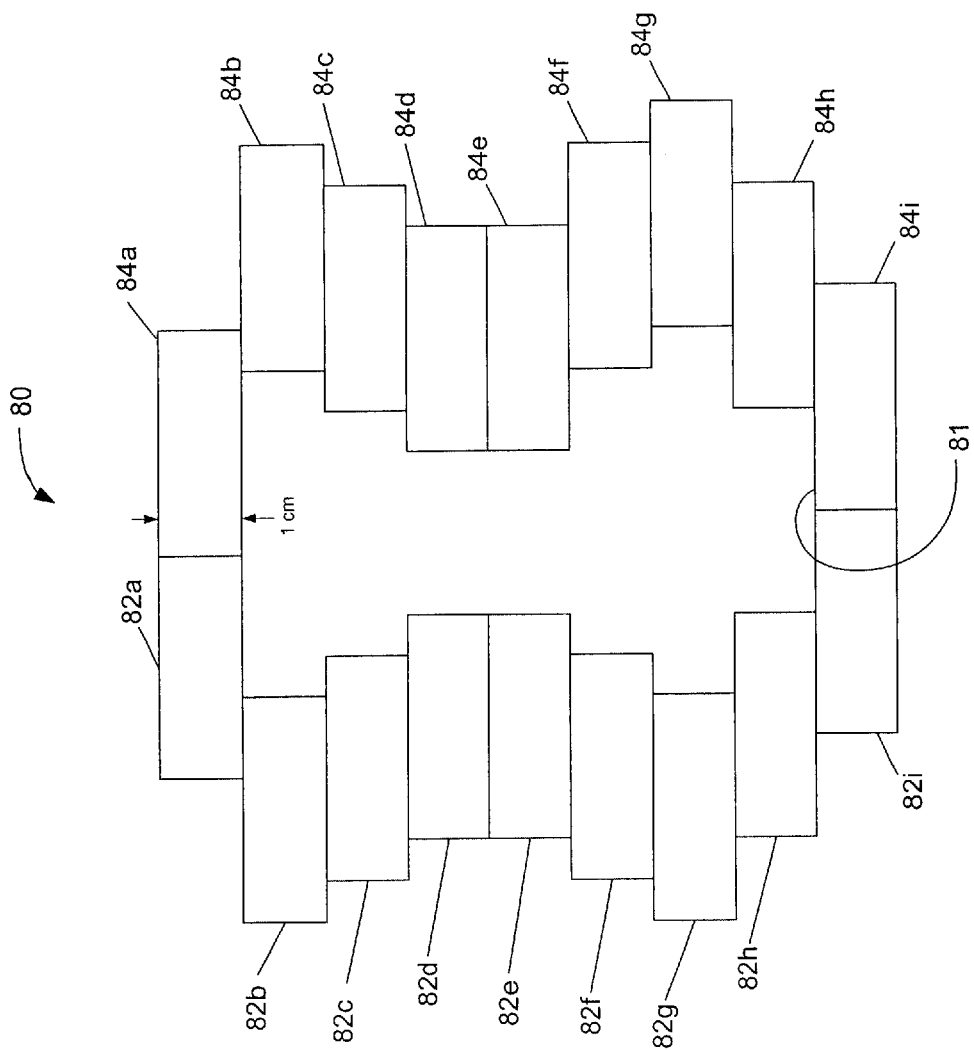
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the process described below.

In order to develop a treatment plan, a field is defined on an object for radiation. The field is divided into multiple segments, each segment having defined parameters. Each of the segments is individually treated with radiation by defining an opening between the radiation source and the object and by generating a radiation beam. The opening is capable of delimiting the radiation beam to the defined parameters of each segment. The treatment is done for each of the segments until the radiation treatment is complete.

Figure 4:
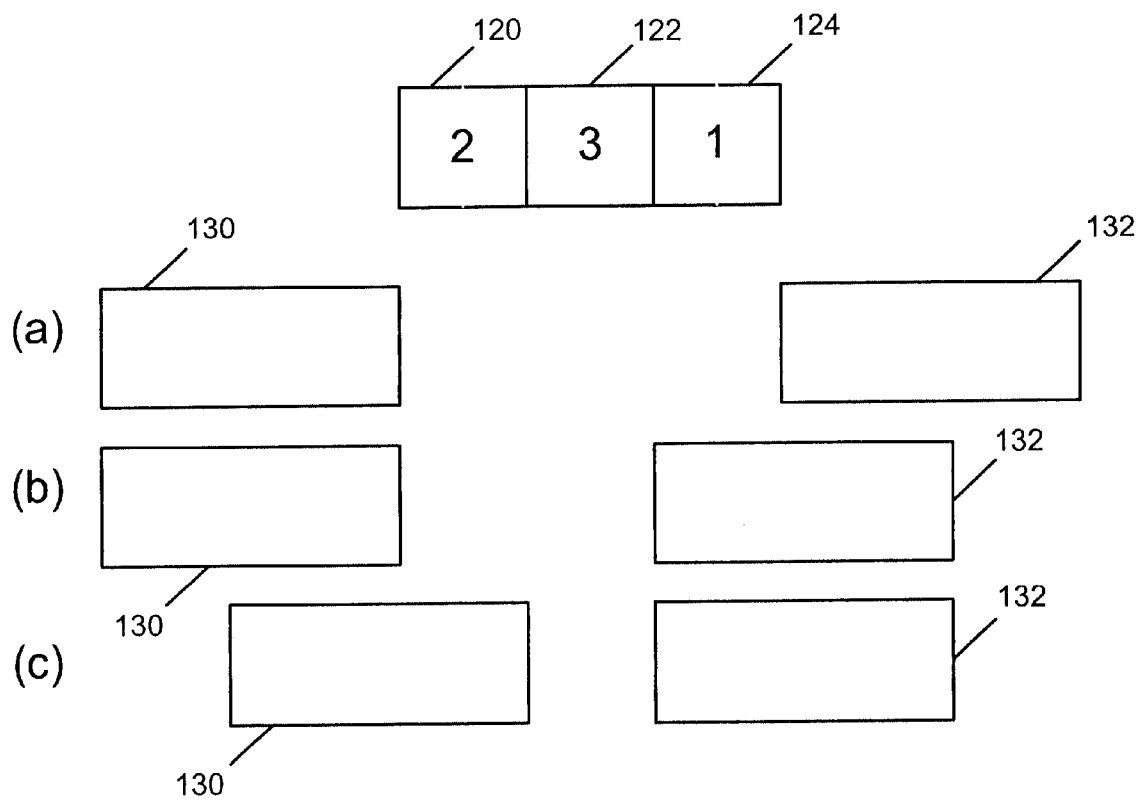
FIG. 4 is a plan view illustrating leaf positions for an exemplary intensity map.

FIG. 4 shows an example of an intensity map comprising three cells 120, 122, 124. The numbers (2, 3, 1) within each cell 120, 122, 124, respectively, represent the radiation intensity level for locations within the field and are in monitor units (mu) or relative monitor unit intensities (e.g., $1 \times 10^2$ mu). The radiation treatment may be applied in three separate intensity (treatment) fields. The treatment shown includes three segments (a), (b), (c) with each segment utilizing one leaf pair having a left position and a right position. The first treatment is shown in the top row labeled (a). An opposing leaf pair 130, 132 is positioned such that one unit of radiation is delivered to all three cells. The leaves 130, 132 are next positioned as shown in row (b). The right leaf (as viewed in FIG. 5a) is moved to the left to cover cell 124 since that cell has already received its required dosage of radiation. The third intensity field labeled (c) allows radiation to be delivered only to the cell 122 since that cell requires three monitor units of radiation.

As previously discussed, some treatment planning systems do not export intensity maps, but only segments. The present invention describes a method for reconstructing the intensity map from imported segments so that this data may be used with segmentation software such as IMFAST.

In order to reconstruct the intensity map, the map geometry must first be determined, if not already known. The map geometry is defined by determining the number of row and columns, and the width of the rows and columns. This can be accomplished by inspecting the leaf positions for all the segments from a given beam direction (i.e., segments having the same gantry, collimator, and couch angles). Since the segments are assumed to be compatible with the multi-leaf collimator that is specified to deliver them, the information about the width of the row can be found from the multi-leaf collimator leaf width. The first open leaf pair and the last open leaf pair can also be identified by inspecting all of the segments. This information is used to determine the number of rows in the intensity map. The information about which row contains the isocenter can also be determined from which leaf pair of the multi-leaf collimator passes over the isocenter. This provides the row geometry for the intensity map. For example, in a typical file containing the segment information, if there are only two segments having a gantry angle, collimator angle and couch angle set to zero, these two segments may be combined to create an intensity map. If the first segment shows leaf pairs 1 to 5 closed, 6 to 10 open and 11 to 29 closed, while the second segment shows 1 to 7 closed, 8 to 15 open, and 16 to 29 closed, then the intensity map used to describe the combination of these segments needs to allot rows corresponding to the first open leaf pair among all segments up to the last open leaf pair among all segments. In this example, that means we need rows for leaf pairs 6 to 15. In the file containing the segment information, there is also information on the type of multi-leaf collimator used. Each collimator type has its own leaf pair number assigned to the isocenter, and in one example this is leaf pair 15. In this example, the leaf pair is positioned such that the isocenter would be covered right at the center of the leaf. Hence the row geometry requires that the row corresponding to leaf pair 15 be the isocenter row, and that the isocenter should be centered inside the row and not on the gridline between rows. Alternate multi-leaf collimator designs may have the edge of a leaf pair over the isocenter, and in that case, the intensity map would need the isocenter to be on the gridline between two rows. In the case of the above example, since leaf pairs 6 to 15 are open, (15−6+1=) 10 rows are needed in the intensity map, and since leaf pair 15 has the isocenter at the center of the leaf pair, the isocenter should be located in the center of the $10^{th}$ row in the map. Finally, since each multi-leaf collimator has its own leaf width, knowing the type of multi-leaf collimator allows one to determine the leaf width, and hence the row width. For example, the leaf pairs may project a 1 cm wide shadow at the isocenter plane. Hence the rows of the intensity map must be 1 cm wide as well. Knowing the number of rows, the width of the rows, the row containing the isocenter, and whether the isocenter is inside the row or on the gridline between two rows fully specifies the row geometry of the intensity map.]

The following describes a method for determining the column geometry for the intensity map. This is more complex then determining the row geometry since the treatment planning system may round off the column gridline positions to the resolution of the multi-leaf collimator leaves, rather than reporting the leaf positions exactly at the gridline. For example, if the column width is 5 mm, and the isocenter is inside a column, then the gridline positions are at 2.5+5n mm (where n=0, +1, +2, . . . ). However, if the treatment planning system rounds off to a leaf resolution of 1 mm, then the leaf positions are reported as 3+5n mm (where n=0, 1, 2, . . . ) and −3+5n (where n=0, −1, −2. . . ). In this case, all the gridline positions for the original intensity map geometry are offset from the leaf positions by half of the leaf resolution. If the round off is not accounted for, the intensity map geometry is calculated as having column widths of 1 mm instead of 5 mm so that the map gridlines line up with the leaf positions. This results in an incorrect number of columns. In order to avoid this problem, the column spacing is first determined in the positive half and negative half independently of the center (not considering the column space at the isocenter). This results in a column spacing of 5 mm everywhere except the isocenter, which is 6 mm, and is different from the other column spacing only by the leaf resolution. If such a condition is found, then the column spacing is set to 5 mm, thus avoiding the round off problem.

Another concern is that the leaf positions may be masked off at a boundary (e.g., an absolute square beyond which there should be no radiation). (See, for example, U.S. patent application Ser. No. 09/649,286, filed Aug. 23,2000). If the location of the mask does not fall on an expected gridline, then it is difficult to calculate the column spacing. For example, if in the previous example, there is a requirement that no leaves are positioned beyond 5 cm, then the leaf position at 4.75 cm is allowable, but a leaf position at 5.25 cm must be moved to 5 cm. Thus, the smallest column space that is found between successive leaf positions is 0.25 cm or 2.5 mm, instead of the 5 mm previously found. If the mask position is not excluded in the analysis to determine the column spacing, it is necessary to look for a map that is consistent with the mask position as well. In this case, that would require a spacing of 2.5 mm instead of 5 mm, even though this space only occurs at the outer edge of the intensity map. To account for this, the farthest leaf positions are excluded from the analysis in the determination of the map column spacing and the mask information is stored and used later when segments are created from the recalculated intensity map. This prevents the calculated leaf positions from exceeding the boundary.

The following examples illustrate determination of column geometry from a given set of segments. Table I lists sample input values for the first example.

TABLE I

| Leaf Pair # | Segment A | | Segment B | |
|---|---|---|---|---|
| | Left Position | Right Position | Left Position | Right Position |
| 1 | −8 | 5 | −5 | 10 |
| 2 | 5 | 10 | 2 | 17 |

The maximum extent of leaf positions for each leaf among all leaf segments is first identified. This creates the mask segment shown in Table II.

TABLE II

| Leaf Pair # | Mask Segment | |
|---|---|---|
| | Left Position | Right Position |
| 1 | −8 | 10 |
| 2 | 2 | 17 |

Next, a list of all leaf positions, excluding the mask segment, is made, as shown in Table III.

TABLE III

| Leaf Pair # | Segment A | | Segment B | |
|---|---|---|---|---|
| | Left Position | Right Position | Left Position | Right Position |
| 1 | | 5 | −5 | |
| 2 | 5 | 10 | | |

The list of leaf positions is analyzed by first determining all of the intervals between all the leaf positions, excluding the interval formed across the isocenter. This results in the following leaf position list for the above Tables:

−5, 5, 10

Since all intensity map geometries are symmetric with respect to the isocenter, the intervals are created by folding the negative list into the positive list and making a new list which combines the absolute values of all the leaf positions (excluding the mask). This results in the following leaf position list which is used to obtain the interval list:

5, 10

This list is then sorted from lowest to highest values and the differences between successive numbers on the list (the intervals) are collected into another list:

10−5=5

The lowest number in the list of leaf positions is doubled and the result added to the interval list:

2*minimum(5,10)=10

This takes care of the interval across the isocenter. The list of intervals is then sorted and repeated values are removed from the list, resulting in the final interval list:

5, 10

Once the interval list is generated, the elements of the list are examined in order to obtain the greatest common factor among the numbers in the list. This is accomplished by taking the first two elements in the list, applying Euclid's algorithm, and then using the result of Euclid's algorithm as a seed to be used with the next element in the list to be put into Euclid's algorithm to get a new seed. This process continues until the list is empty, and the final pass of Euclid's algorithm gives the greatest common factor of the list. In order to deal with the round off situation described above, Euclid's algorithm is modified so that the iterations stop when a tolerance value equal to the leaf resolution is reached (instead of the usual termination criterion in the algorithm that the tolerance is zero). The result is the column size. For the above interval list, application of Euclid's algorithm results in a column size of 5.

Next, it needs to be determined if the isocenter falls inside a column or on a column gridline. This is done by taking the first leaf position in the leaf position list (excluding the mask segment) and dividing it by the column size. If there is a remainder, the isocenter falls inside the column. If there is no remainder, the isocenter falls on a gridline. For the above example, all of the numbers in the leaf position list are integral multiples of the column size. Thus, the isocenter must be on a gridline.

With the column size and the location of the isocenter known, the mask segment is used to find the widest extent of the mask. The left and right side values of the mask are then rounded off to the nearest column gridline outside of the mask. These values are then used to calculate the number of columns. From the above mask segment (Table III), the minimum value is −8 and the maximum value is 17. The gridlines for the intensity map are at 5n (where n is an integer) since the column size is 5 and the isocenter (the zero value) is on a gridline. Thus, one value of 5n must be smaller than −8 and another value of 5n must be larger than 17. This results in values of −10 and 20. The gridlines of the intensity map therefore have the following values:

−10, −5, 0, 5, 10, 15, 20

Since there are 7 gridlines, there must be 6 columns, with the isocenter located at the left edge of the third column. The first column spans the space between the gridlines at −10 and −5, the second column spans the space between the gridlines at −5 and 0, with the isocenter at 0, on the right edge of the second column, and the third column spans the space between the gridlines at 0 and 5, with the isocenter at 0, on the left edge of the third column.

The following example illustrates calculations for an intensity map having an isocenter inside of a column. The following tables show the input values (Table IV), mask segment (Table V), and leaf positions excluding the mask (Table VI).

TABLE IV

| | Segment A | | Segment B | |
| --- | --- | --- | --- | --- |
| Leaf Pair # | Left Position | Right Position | Left Position | Right Position |
| 1 | −15 | 5 | −5 | 25 |
| 2 | −45 | 15 | −35 | 55 |

TABLE V

| | Mask Segment | |
| --- | --- | --- |
| Leaf Pair # | Left Position | Right Position |
| 1 | −15 | 25 |
| 2 | −45 | 55 |

TABLE VI

| | Segment A | | Segment B | |
| --- | --- | --- | --- | --- |
| Leaf Pair # | Left Position | Right Position | Left Position | Right Position |
| 1 | | 5 | −5 | |
| 2 | | 15 | −35 | |

The leaf position list (excluding the mask segment) is:
−35, −5, 5, 15
The leaf position list to be used in finding the interval list is obtained by taking the absolute values of the leaf position list and placing them in numerical order: 5, 15, 35
Since there are three values in the leaf position list, no special processing is needed and the interval list is calculated as follows:
Interval list: 15−5=10
35−15=20
Next, Euclid's algorithm is applied to the numbers 10 and 20 to get their greatest common factor, which is 10. The column size is therefore 10.
The smallest value in the leaf position list is 5. Since this is not an integral multiple of 10, the isocenter is located inside of a column and is offset by half of a column.
From the mask segment, the minimum value is −45 and the maximum value is 55. The gridlines of the intensity map are at 10n+5 (where n is an integer) since the column size is 10 and the isocenter (the zero value) is offset by 5. Thus, one value 10n+5 is needed that is smaller than or equal to −45. Another value of 10n+5 is needed that is larger than or equal to 55. The two additional values are −45 and 55. The gridlines of the intensity map therefore have the values −45, −35, −25, −15, −5, 5, 15, 25, 35, 45, 55. Since there are 11 gridlines, there are 10 columns, with the isocenter being inside the fifth column.

Once the segments (that have common gantry, collimator, and couch angles) and a known intensity map geometry is available, the contribution from the primary beam for a given segment may be determined for each cell in the intensity map by determining if the cell is obscured by any leaves in the segment. If the cell is not blocked, it receives the primary contribution, weighted by the number of monitor units (mu) that the particular segment uses to expose the intensity map. Thus, the primary contribution can be determined for each cell in the intensity map for each segment, and the contributions from each segment can be summed to get the total primary contribution.

In order to obtain the leakage contribution, the opposite process is performed. If a given cell is under a leaf for a given segment, then that cell receives the leakage contribution, weighted by the number of monitor units that the particular segment uses to expose the map. The calculation is done for each cell in the map for each segment, and the contributions from each segment added together to get the total leakage contribution.

For scatter contribution, ray tracing may be performed as described in U.S. Pat. Nos. 6,167,114 and 6,108,400, which are incorporated herein by reference in their entirety, or any other suitable method. The calculations are done for each segment. The summation of the contributions for each segment provides the total scatter contribution. The finite size of the source may be accounted for and multiplied by the primary term of the scatter contribution. The process for accounting for the finite source size is described in U.S. patent application Ser. No. 09/648,193, filed Aug. 23, 2000.

The sum of the primary, leakage, and scatter contributions provide a calculated intensity map. In the case where an original intensity map is also known, an error map can be calculated as well and fluence error reduction can be performed, as described in U.S. Pat. No. 6,128,366, which is incorporated herein by reference in its entirety. In the case where any original intensity map is not provided, the purpose of calculating the map is to provide a map which can serve as the input intensity map that can be converted into a more efficient set of segments, as described in U.S. Pat. No. 5,663,999, which is incorporated herein by reference in its entirety.

If the intensity map is to be discrete, then after the initial calculations described above, the values in the map need to be rounded off to the nearest discrete values required by the treatment planning system. If the intensity map is to be a description of the primary and leakage values only, the scatter component should be excluded. Thus, the calculation of the intensity map for the purpose of matching the intensity map that the treatment planning system used to generate the input segments requires flexibility. This is achieved by utilizing a configuration file at the time that the segments are imported. This file preferably specifies the components of the calculations that need to be included, as well as any other parameters that may be known about the original intensity map that is being reconstructed (e.g., number of discrete levels). These can then be taken into account when the map is calculated from the segments and the appropriate components can be included. Also, any post calculation steps such as rounding off to the nearest level can be performed.

Figure 5:
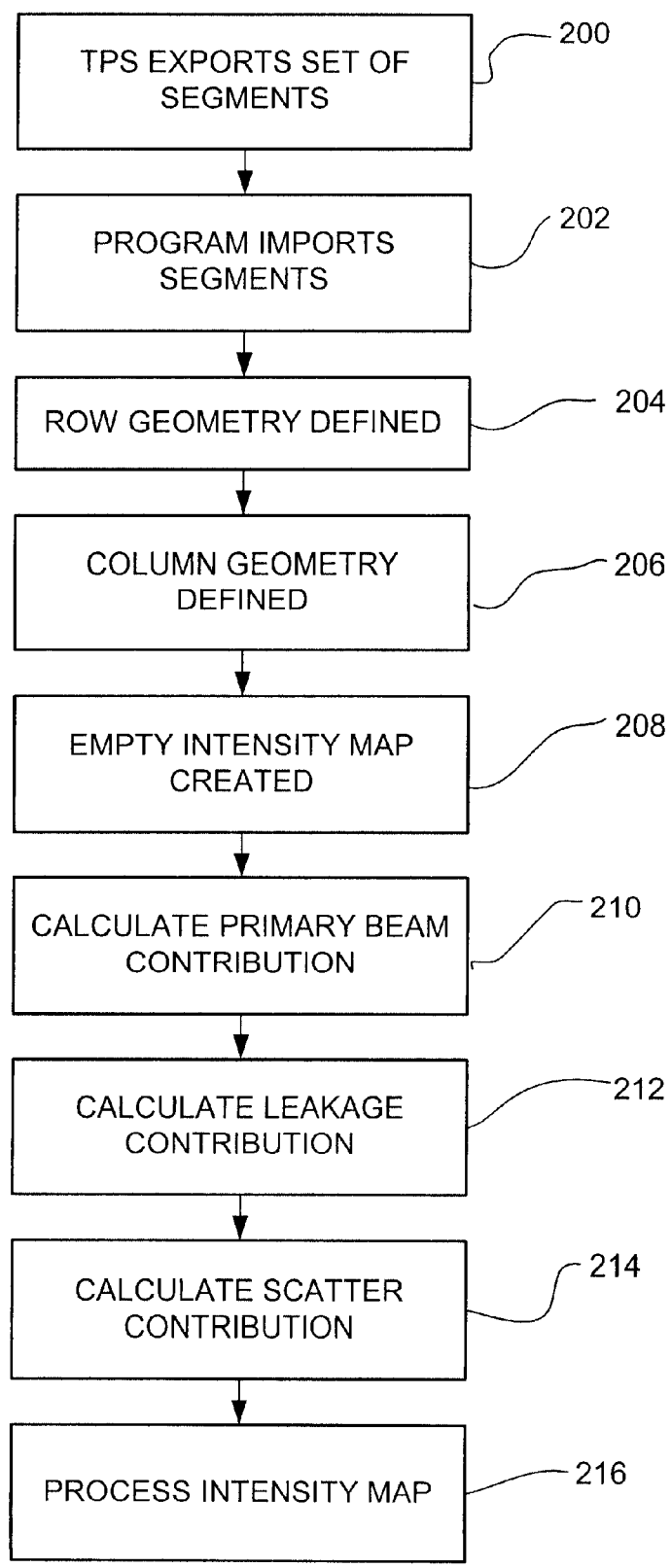
FIG. 5 is a flowchart illustrating a process for reconstructing an intensity map from segments.

FIG. 5 is a flowchart illustrating a process for reconstructing an intensity map from segments. The treatment planning system first exports a set of segments which make up the intensity modulated treatment at step 200. The program that uses the intensity map imports the segments (step 202) and analyzes the segments to get the map geometry. The segments imported may be for any treatment that has a multiple number of segments with the same gantry, collimator, and couch positions. The treatment does not have to be produced by a treatment planning system that specifically created the segments for intensity modulated radiation therapy. For example, a "field-in-field" or concomitant boost plan that would have such segments may be used.

The row geometry is first determined at step 204. The column geometry is then analyzed as described above (step 206). An empty intensity map is created from the geometry with the correct number of rows and columns and row and column width (step 208). For each location in the map, the appropriate radiation contributions from each segment are calculated. This includes contribution from the primary beam (step 210), leakage contribution (step 212), and scatter contribution (step 214). The intensity map is then processed (i.e., rounded off to the nearest discrete levels) and fed into a data structure that holds this final calculated intensity map (step 216). From this point, the program only needs to work with the intensity maps and does not have to store the segments, although it may store the segments to use in an alternative segmentation method.

It is to be understood that the method may vary from the above description without departing from the scope of the invention. For example, assumptions about the intensity map geometry may be made up front rather than deriving the entire geometry from the segments. It may be assumed, for example, that there are no round off problems due to leaf resolution errors and no masking occurs. The rest of the geometry may then be derived from leaf positions.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for reconstructing an intensity map from segments, the method comprising:

importing a set of segments;

analyzing the segments to determine intensity map geometry;

calculating radiation contributions for cells within the segments; and creating a reconstructed intensity map.

2. The method of claim 1 wherein calculating radiation contributions comprises calculating primary beam contributions.

3. The method of claim 2 wherein calculating primary beam contributions comprises determining if any of the cells are not blocked by a leaf for each of the segments.

4. The method of claim 1 wherein calculating radiation contributions comprises calculating leakage contributions.

5. The method of claim 4 wherein calculating leakage contributions comprises determining if any of the cells are blocked by a leaf for each of the segments.

6. The method of claim 1 wherein calculating radiation contributions comprises calculating scatter contributions.

7. The method of claim 6 wherein calculating scatter contributions comprises performing ray tracing for each of the segments.

8. The method of claim 1 wherein calculating radiation contributions comprises calculating primary beam contribution, leakage contribution, and scatter contributions.

9. The method of claim 8 wherein an intensity map is imported along with the segments and further comprising performing fluence error reduction.

10. The method of claim 1 wherein analyzing the segments to determine the intensity map geometry comprises determining the number of rows and columns in the intensity map.

11. The method of claim 10 wherein determining the number of rows comprises defining a first open leaf pair and a last open leaf pair based on the imported segments.

12. The method of claim 10 wherein determining the number of rows comprises defining a row containing an isocenter by identifying a leaf pair that passes over the isocenter.

13. The method of claim 10 wherein determining the number of columns comprises defining a mask segment.

14. The method of claim 13 further comprising defining an interval list based on the imported segments and the mask segment.

15. The method of claim 14 further comprising applying Euclid's algorithm to the interval list to find the greatest common factor in the interval list.

16. The method of claim 1 wherein determining intensity map geometry comprises determining whether an isocenter of the map falls inside a column or an a column gridline.

17. A system for reconstructing an intensity map from segments, the system comprising a processor configured to import a set of segments and operable to analyze the segments to determine intensity map geometry, calculate radiation contributions for each cell in each of the segments, and create a reconstructed intensity map; and memory operable to at least temporarily store the segments.

* * * * *